United States Patent [19]

Williams

[11] Patent Number: 4,973,717

[45] Date of Patent: Nov. 27, 1990

[54] PRODUCTION OF ALCOHOLS AND ETHERS BY THE CATALYSED HYDROGENATION OF ESTERS

[75] Inventor: Peter S. Williams, Hedon, England

[73] Assignee: BP Chemicals Limited, London, England

[21] Appl. No.: 438,433

[22] PCT Filed: May 4, 1989

[86] PCT No.: PCT/GB89/00469

§ 371 Date: Dec. 1, 1989

§ 102(e) Date: Dec. 1, 1989

[87] PCT Pub. No.: WO89/10911

PCT Pub. Date: Nov. 16, 1989

[30] Foreign Application Priority Data

May 10, 1988 [GB] United Kingdom ............... 8811009

[51] Int. Cl.$^5$ .................... C07C 29/147; C07D 307/08
[52] U.S. Cl. ..................................... 549/508; 568/864
[58] Field of Search .......................... 549/508; 568/864

[56] References Cited

U.S. PATENT DOCUMENTS

| | | | |
|---|---|---|---|
| 4,096,156 | 6/1978 | Freudenberger | 260/343.6 |
| 4,104,478 | 8/1978 | Trivedi | 568/885 |
| 4,105,674 | 8/1978 | DeThomas | 260/343.6 |
| 4,301,077 | 11/1981 | Pesa et al. | 549/508 |
| 4,524,225 | 6/1985 | Qualeatti | 568/885 |
| 4,609,636 | 9/1986 | Mabry et al. | 502/183 |
| 4,611,085 | 9/1986 | Kitson | 568/885 |
| 4,772,729 | 9/1988 | Rao | 549/326 |
| 4,804,791 | 2/1989 | Kitson | 568/885 |
| 4,827,001 | 5/1989 | Attig et al. | 549/326 |

FOREIGN PATENT DOCUMENTS

| | | |
|---|---|---|
| 147219 | 7/1985 | European Pat. Off. . |
| 0177393 | 9/1985 | European Pat. Off. . |
| 285420 | 10/1988 | European Pat. Off. . |
| 1551741 | 4/1976 | United Kingdom . |
| 1534232 | 2/1977 | United Kingdom . |

OTHER PUBLICATIONS

Journal of the Less-Common Metals, 89 (1983), 522–535, 1983 Gryaznov et al.

Journ. Chem. Tech. Biotechnol. 1987, vol. 37, pp. 257–270, Thomson et al.

*Primary Examiner*—Richard L. Raymond
*Attorney, Agent, or Firm*—Brooks, Haidt, Haffner & Delahunty

[57] ABSTRACT

An alcohol and/or an ether is produced from a carboxylic acid ester by reacting the ester with hydrogen at elevated temperature in the presence as catalyst of a composition comprising an alloy of (i) at least one noble metal of Group VIII of the Periodic Table of the Elements and (ii) at least one metal capable of alloying with the aforesaid Group VIII noble metal.

9 Claims, No Drawings

PRODUCTION OF ALCOHOLS AND ETHERS BY THE CATALYSED HYDROGENATION OF ESTERS

This present invention relates in general to the production of alcohols and ethers by the catalysed hydrogenation of esters and in particular to the production of $C_4$ alcohols and ethers by the catalysed hydrogenation of either the esters of $C_4$ dicarboxylic acids or gamma-butyrolactone.

Alcohols and ethers are valuable industrial products which find wide useage as solvents.

The use of heterogeneous catalysts in the hydrogenation of esters is known.

A problem associated with the use of heterogeneous hydrogenation catalysts in ester hydrogenation reactions is the simultaneous co-production of unwanted alkanes, e.g. methane and ethane, by side reactions, thereby decreasing the overall selectivities to alcohols and/or ethers.

Our copending European application No. 88302891.2 (BP Case No. 6544) discloses the production of an alcohol and/or a carboxylic acid ester from a carboxylic acid or anhydride thereof by reacting the acid or anhydride with hydrogen at elevated temperature in the presence as catalyst of a composition comprising an alloy of (i) at least one noble metal of Group VIII of the Periodic Table and (ii) at least one metal capable of alloying with the Group VIII noble metal, for example either silver, gold or copper, and optionally including a support and at least one of the metals rhenium, tungsten or molybdenum.

We have now found that the problem of alkane formation in ester hydrogenation can be substantially reduced by using the alloy catalyst of our aforesaid copending European application.

Accordingly, in one aspect the present invention provides a process for the production of an alcohol and/or an ether from a carboxylic acid ester which process comprises reacting the ester with hydrogen at elevated temperature in the presence as catalyst of a composition comprising an alloy of (i) at least one noble metal of Group VIII of the Periodic Table of the Elements, and (ii) at least one metal capable of alloying with the aforesaid Group VIII noble metal.

Hydrogen is commercially available on a large scale and may be used with or without further purification. A desirable purification may be removal of carbon monoxide.

The process of the invention is applicable to the hydrogenation of carboxylic acid esters, which term includes not only the open-chain esters, for example ethyl acetate, but also cyclic internal esters, for example gamma-butyrolactone. Suitable open-chain carboxylic acid esters are esters of $C_1$ to $C_{24}$ acyclic mono- or di-, saturated or unsaturated, straight-or branched-chain carboxylic acids. Suitably the esters are alkyl esters, preferably lower, i.e. $C_1$ to $C_4$, alkyl esters. Suitable cyclic internal esters include $C_5$ to $C_7$ lactones. Examples of carboxylic acid esters useful herein include but are not in any way to be limited to methyl acetate, ethyl acetate, propyl acetate, butyl acetate, dimethyl maleate, dimethyl succinate, methyl methacrylate, methyl oxalate and gamma-butyrolactone.

As regards the catalyst composition, the noble metals of Group VIII of the Periodic Table of the Elements are palladium, platinum, rhodium, ruthenium, osmium and iridium. Of the aforesaid noble metals, palladium, rhodium and ruthenium are preferred. Metals capable of alloying with palladium include silver, gold, copper, nickel, rhodium, tin, cobalt, aluminium, manganese, gallium, iron, chromium and platinum, of which silver, gold and copper are preferred. Metals capable of alloying with ruthenium include iron, cobalt, manganese, germanium and rhenium.

Although a catalyst composition comprising an alloy of (i) at least one noble metal of Group VIII of the Periodic Table of the Elements, and (ii) at least one metal capable of alloying with the aforesaid Group VIII noble metal (hereinafter to be designated component (A)) may be used as catalyst in the hydrogenation of carboxylic acid esters, it is preferred to employ a catalyst incorporating one or more further components.

It is preferred to incorporate (as component (B)) at least one of the metals rhenium, tungsten or molybdenum.

It is preferred to incorporate a support (as component (C)). Suitable supports include high surface area graphitised (HSAG) carbons, graphites, activated carbons, silicas, aluminas and silica/aluminas, of which HSAG carbons and high surface area silicas and aluminas are preferred.

Particularly suitable supports are the high surface area graphitised carbons described in GB-A-2136704, the disclosure of which is incorporated herein by reference.

Preferred silica and alumina supports are those having a high surface area, typically greater than 50 $m^2/g$.

Suitably the catalyst composition comprises from 0.1 to 20% by weight, preferably from 1 to 10% by weight of component (A), from 0.1 to 20% by weight, preferably from 1 to 10% by weight of component (B), the remainder of the catalyst comprising a support.

The catalyst composition may be further modified by incorporation of a metal or metals of Group IA, Group IIA, or Group IVA.

The alloy constituting component (A) of the catalyst composition of the present invention may be produced in any suitable manner, for example thermally or by a colloidal method. The component (A) may then be admixed with component (B). Components (A) and (B) may be applied to a support either individually or in combination by conventional means.

A supported catalyst composition as hereinbefore described may suitably be produced by a process comprising the steps (i) depositing on a support at least one noble metal compound and a compound of at least one metal capable of forming an alloy with the Group VIII noble metal, said compounds being thermally decomposable/reducible to the metal, (ii) heating the composition obtained in step (i) under conditions and at a temperature such that the compounds are thermally decomposed/reduced to the metals and form an alloy thereof, and (iii) depositing on the composition obtained in step (ii) a compound of at least one of ths metals rhenium, tungsten or molybdenum.

A preferred process for producing a supported catalyst composition as hereinbefore described comprises the steps of:

(I) impregnating a support with a solution or solutions of (i) at least one soluble Group VIII noble metal compound thermally decomposable/reducible to the noble metal and (ii) a soluble compound thermally decomposable/reducible to the metal of at least one metal capable of alloying with the Group VIII noble metal and removing the solvent therefrom, (II) heating the composition obtained in step (I) under conditions and at a temperature such that the compounds are thermally decomposed/reduced to the metals and form an alloy thereof, and (III) impregnating the composition obtained in step (II) with a compound of at least one of the metals rhenium, tungsten or molybdenum and removing the solvent therefrom.

The solvent used in steps (I) and (III) of the process may be the same or different, preferably the same, and may be any suitable solvent, for example water.

Techniques for impregnating supports with solutions of metal compounds and removing ths solvent therefrom are well known in the art and require no further elaboration. Such techniques include the incipient wetness technique and the excess solution technique.

In step (II) the composition may suitably be heated at a temperature above about 600° C. to thermally decompose/reduce thermally decomposable/reducible compounds of the metals to the elemental metals and produce alloys thereof. This heating step ma suitably be accomplished in the presence of an inert gas, for example nitrogen. Although about 600° C. is indicative of the temperature at which palladium and silver must be heated to form the alloy, the optimum temperature will depend on the nature of the particular combination of metals involved.

Preferably, a further step is interposed between step (I) and step (II) and optionally following step (III) wherein the impregnated support is dried, suitably by heating at a temperature in the range from 50 ° to 150° C. It will be appreciated by those skilled in the art that this step may be incorporated into step (II), if desired.

Following step (III) there may be incorporated a further step (IV) wherein thermally decomposable/reducible compounds of at least one of the metals rhenium, tungsten or molybdenum is (are) thermally decomposed/reduced to the metallic form. Alternatively, this may be accomplished in a catalyst activation step.

Suitable molybdenum, tungsten or rhenium compounds which are decomposable/reducible to the metal and/or oxide include salts of the metals and salts wherein the metals are present in the anionic moiety, for example, ammonium molybdate or ammonium tungstate. Suitable noble metal compounds which are decomposable/reducible to the noble metal include, for example, noble metal salts such as the carboxylates, halides and nitrates and ammonium salts containing the noble metal in the anion moiety, for example ammonium tetrachloropalladate. Suitable compounds of metals capable of alloying with a noble metal include salts of the metals, for example nitrates, carboxylates and halides.

The metal of Group IA, Group IIA or Group IVA of the Periodic Table of the elements may be added to the catalyst composition at any point during its preparation. Thus, the supported alloy composition may be impregnated with a solution of a soluble compound of the metal. Alternatively, a soluble compound of the metal may be added to the impregnation solutions.

A preferred catalyst comprises (i) an alloy of palladium and silver, and (ii) rhenium supported on a high surface area graphitised carbon of the type described in the aforesaid GB-A-2136704.

Before use in the process of the invention the catalyst is preferably activated by contact at elevated temperature with either hydrogen or a hydrogen/inert gas, for example nitrogen mixture, suitably for a period of from 1 to 20 hours. The elevated temperature may suitably be in the ranges from 200° to 350° C. Alternatively, the catalyst may ba activated by heating to the reaction temperature in the presence of reactants.

The process may be operated in the liquid phase or the vapour phase and either batchwise or continuously, preferably continuously. The catalyst may be employed in the form of a fixed bed, a moving bed or a fluidised bed.

It is an advantage of ths process of the present invention that the selectivity of ester hydrogenation to desired products (alcohol/ether) can be increased at the expense of undesirable products (alkanes).

The process of the present invention is particularly applicable to the hydrogenation of the esters of $C_4$ dicarboxylic acids and gamma-butyrolactone.

In another aspect therefore the present invention provides a process for the production of a product comprising tetrahydrofuran and 1,4-butanediol from either an ester of a $C_4$ dicarboxylic acid or gamma-butyrolactone which process comprises reacting the ester or gamma-butyrolactone at elevated temperature with hydrogen in the presence as catalyst of component (A) as hereinbefore described.

Carboxylic acids which in the form of their esters may be used as reactants in the process for the production of a product comprising tetrahydrofuran and 1,4-butanediol include maleic acid and succinic acid.

Component (A) preferably comprises either palladium, ruthenium or rhodium, more preferably palladium as the noble metal (i) and either silver, gold or copper as ths metal (ii) capable of alloying with palladium. Component (A) may be used as catalyst either with or without the hereinbefore described components (B) and (C), though the presence of component (C), i.e. a support, is preferred. A preferred support is an HSAG carbon as hereinbefore described.

The catalyst is preferably activated before use in the process by the method as hereinbefore described.

The process may be operated batchwise or continuously and the ester or gamma-butyrolactone may be introduced in either the liquid phase or the vapour phase. In the liquid phase it is preferred to use a solvent. As the solvent there may be used either water and/or an inert organic solvent, for example 1,4-dioxane.

As regards ths reaction conditions, the temperature may suitably be in the range from 50° to 350° C., preferably 150° to 300° C., and the pressure may suitably be in the range from 1 to 300 barg, preferably 10 to 150 barg. The Liquid Hourly Space Velocity (LHSV) for continuous operation may suitably be in the range from 0.05 to 10, preferably from 0.1 to 5. The gas to liquid ratio for liquid phase operation may suitably be in the range from 1:300, preferably from 1:100.

The invention will now be further illustrated by reference to the following Examples and Comparison Test.

In the following Examples and Comparison Tests the term "HSAG carbon" denotes high surface area graphitised carbon, prepared and characterised as follows:

The carbon used as support was prepared from a commercially available activated carbon sold by Ceca under the designation Acticarbone ACL40. The activated carbon was heat treated as follows. The carbon was heated from room temperature in a stream of nitrogen to 1700°–1800° C. over a period of about one hour. The temperature was held at 1700°–1800° C. for about twenty minutes then the carbon was cooled to room temperature. A water cooled heat exchanger was used to lower the temperature in a period of one hour. The carbon was then heated in air in a rotating kiln furnace at approximately 520° C. for a time known from experience to give a weight loss of 20% wt at a rate of less than 5% wt per hour. The carbon was then heated in nitrogen to between 1700° C. and 1800° C. and cooled to room temperature in a nitrogen atmosphere. The resulting graphite-containing carbon was then crushed to 16–30 mesh BSS.

The resulting carbon had the following properties:
BET surface area: 6∞m²/g
Basal plane surface area: 460 m2/g
Edge surface area: 8 m²g
BET/basal surface area ratio: 1.36 m²/g
Basal plane/edge surface area ratio: 58

The carbon was then refluxed in 5% hydrochloric acid in aqueous solution for 2–3 hours, filtered and washed with distilled water. It was refluxed in distilled water for 2–3 hours, filtered and dried overnight in a vacuum oven at 100° C.

CATALYST PREPARATION - PALLADIUM BASED CATALYSTS

Nominal loading is defined as weight of metal (not salt) added to the support expressed as a percentage of the weight of support.

Catalyst A

An aqueous solution containing dissolved palladium nitrate was added to HSAG. The water was removed on a rotary evaporator, and the resulting impregnated carbon was dried at 150° C. in an oven overnight. The amount of palladium nitrate was chosen to give a nominal loading of 3% Pd. Ths catalyst was then cooled and transferred to a glass tubs, and was heated in a stream of nitrogen using the following conditions: from room temperature to 300° C. over a period of eight hours then eight hours at 300° C. followed by cooling to room temperature in nitrogen.

This composition was then mixed with an aqueous solution of rhenium heptoxide, ths solvent again removed on a rotary evaporator, and the composition dried overnight in an oven at 150° C. to give a catalyst of nominal loading -3% Pd -3% Re.

This is not an example of a catalyst suitable for use in the process of the present invention because it does not contain an alloyed metal component. It is included only for the purpose of comparison.

Catalyst B

The procedure used for the preparation of Catalyst A was repeated except that silver nitrate was added to the solution of palladium nitrate. The amounts of the various components were chosen to give a composition with nominal loadings as follows 1.54% Ag, 3% Pd, 3% Re . A second difference was that the composition before the addition of rhenium was heated in a stream of nitrogen using the following conditions: from room temperature to 600° C. over a period of eight hours, then eight hours at 600° C. followed by cooling to room temperature in nitrogen.

Catalyst C

Ths procedure used for the preparation of Catalyst B was repeated to give a composition of nominal loading: 3% Pd -3.07% Ag - 3% Re.

Catalyst D

The procedure used for the preparation of Catalyst B was repeated to give a composition of nominal loading 3% Pd - 6.14 Ag - 3% Re.

Comparison Test and Examples 1 to 3

A 300 ml stainless steel autoclave was purged with nitrogen and then charged with catalyst (1.0 g) and a solution containing gamma-butyrolatone (17.56 g ), water (3.67 g ) and 1,4-dioxane (145.77 g). The autoclave was then purged using hydrogen and then pressurised to 80 barg with hydrogen. Heating and stirring was commenced (5° C./min, 1000 rpm) until 230° C. was attained. This temperature was maintained for twelve hours with continued stirring. After this period the heating stirring was ceased and the autoclave allowed to cool to room temperature. Gas and liquid phases were sampled and analysed by gas-liquid chromatography. Results are reported in the Table.

TABLE

EFFECT OF ALLOYING WITH Ag ON gamma BLO HYDROGENATION

| Catalyst | Example | Ag Loading | Pd:Ag Ratio | Productivity[1] (Kg/kgcat/h) | Selectivity (%) (THF, BDO) | Selectivity (%) | | | | |
|---|---|---|---|---|---|---|---|---|---|---|
| | | | | | | THF | BDO | BuOH | Methane | Butane |
| A | CT | 0 | - | 0.52 | 89 | 88.2 | 0.8 | 0.4 | 10.6 | 11.1 |
| B | 1 | 1.54% | 1:0.5 | 0.13 | 95.9 | 87.9 | 7.9 | 3.6 | 0.5 | 0 |
| C | 2 | 3.07% | 1:1 | 0.09 | (1) | | | | | |
| D | 3 | 6.14% | 1:2 | 0.14 | 96.1 | 90.8 | 5.3 | 3.7 | 0.2 | 0 |

(1) Selectivity data inaccurate due to low conversion
Abbreviations:
THF - tetrahydrofuran
BDO - 1,4-butanediol

I claim:

1. A process for the production of an alcohol and/or an ether from a carboxylic acid ester which process comprises reacting the ester with hydrogen at elevated temperature in the presence as catalyst of a composition comprising a component (A) which comprises an alloy of (i) at least one noble metal of Group VIII of the Periodic Table of the Elements and (ii) at least one metal capable of alloying with the aforesaid Group VIII noble metal.

2. A process according to claim 1 wherein the carboxylic acid ester is either methyl acetate, ethyl acetate, propyl acetate, butyl acetate, dimethyl maleate, dimethyl succinate, methyl methacrylate, methyl oxalate or gamma-butyrolactone.

3. A process according to either claim 1 or claim 2 wherein the noble metal of Group VIII of the Periodic Table is either palladium, rhodium or ruthenium.

4. A process according to claim 1 wherein the catalyst comprises an alloy of palladium and either silver, gold or copper.

5. A process according to claim 3 wherein the catalyst further comprised (as component (B) at least one of the metals rhenium, tungsten or molybdenum.

6. A process according to claim 3 wherein the catalyst incorporates a support which is any of a high surface area graphitised (HSAG) carbon, a graphite, an activated carbon, a silica, an alumina or a silica/alumina.

7. A process according to claim 6 wherein the support is either a silica or alumina having a surface area greater than 50 m$^2$/g or an HSAG carbon.

8. A process according to claim 5 wherein the catalyst composition comprises from 1 to 10% by weight of component (A), from 1 to 10% by weight of component (B), the remainder of the catalyst comprising a support.

9. A process for the production of a product comprising tetrahydrofuran and 1,4-butanediol from either an ester of a C$_4$ dicarboxylic acid or gamma-butyrolactone which process comprises reacting the ester or gamma-butyrolactone at elevated temperature with hydrogen in the presence as catalyst of a composition comprising an alloy of (i) palladium and (ii) either silver, gold or copper.

* * * * *

UNITED STATES PATENT AND TRADEMARK OFFICE
CERTIFICATE OF CORRECTION

PATENT NO. : 4,973,717

DATED : November 27, 1990

INVENTOR(S) : Peter S. Williams

It is certified that error appears in the above-identified patent and that said Letters Patent is hereby corrected as shown below:

Col. 2, l. 57, after "of" and before "metals" correct the spelling of "the"

Col. 3, l. 21, after "step" correct the spelling of "may"

Col. 4, l. 4, before "activated" correct the spelling of "be"

Col. 5, l. 13, should read "628 m$^2$/g"

Col. 5, l. 51, after "glass" correct the spelling of "tube"

Signed and Sealed this

Nineteenth Day of May, 1992

*Attest:*

DOUGLAS B. COMER

*Attesting Officer*  *Acting Commissioner of Patents and Trademarks*